United States Patent [19]

Hübner et al.

[11] 4,136,197

[45] Jan. 23, 1979

[54] HYPOGLYCAEMICALLY AND HYPOLIPIDAEMICALLY EFFECTIVE N-SUBSTITUTED CARBOXYLIC ACID AMIDES

[75] Inventors: Manfred Hübner, Ludwigshafen am Rhein; Ruth Heerdt, Mannheim-Freudenheim; Elmar Bosies, Heppenheim; Hans Kühnle, Mannheim-Neuostheim; Felix H. Schmidt, Mannheim-Seckenheim, all of Germany

[73] Assignee: Boehringer Mannheim GmbH, Mannheim, Germany

[21] Appl. No.: 785,255

[22] Filed: Apr. 6, 1977

[30] Foreign Application Priority Data

Feb. 7, 1976 [DE] Fed. Rep. of Germany ....... 2629752

[51] Int. Cl.² .................... C07C 63/44; A01N 09/20
[52] U.S. Cl. ................................. 424/319; 560/41; 260/558 P; 260/559 R; 260/345.3; 260/327 R; 424/275; 424/278; 424/309; 424/324; 562/442; 562/451
[58] Field of Search ............ 260/518 R, 518 A, 519; 560/38, 39, 41; 424/319

[56] References Cited

U.S. PATENT DOCUMENTS

| 3,536,753 | 10/1970 | Gruenfeld et al. ............ 260/519 |
| 3,839,433 | 10/1974 | Wasley .................... 260/518 R |
| 3,940,422 | 2/1976 | Harita et al. ............... 260/518 R |
| 4,026,896 | 5/1977 | Harita et al. ............... 260/519 |

*Primary Examiner*—James O. Thomas, Jr.
*Assistant Examiner*—James H. Reamer
*Attorney, Agent, or Firm*—Sprung, Felfe, Horn, Lynch & Kramer

[57] ABSTRACT

An N-substituted carboxylic acid amide of the formula

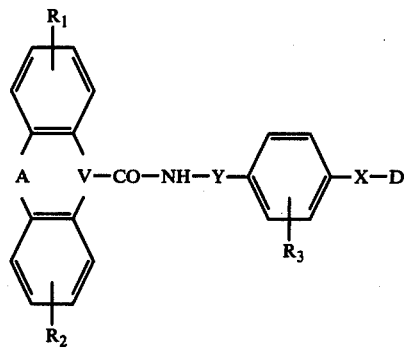

(I)

wherein
A is a valency bond or an oxygen or sulphur atom or a methylene, ethylene, vinylene, ethyleneoxa or ethylenethia radical,
V is a trivalent hydrocarbon radical containing up to 4 carbon atoms,
$R_1$ and $R_2$ each independently is hydrogen, a halogen atom, a hydroxyl group or an alkyl or alkoxy radical,
$R_3$ is hydrogen, a hydroxyl group or an alkoxy radical,
Y is an alkylene radical containing up to 3 carbon atoms,
X is a valency bond or a divalent aliphatic hydrocarbon radical containing up to 6 carbon atoms, and
D is a hydroxymethyl, formyl, free or esterified carboxyl or an N-substituted carbamoyl radical, or a physiologically compatible salt thereof, characterized by hypoglycaemic and hypolipidaemic activity.

16 Claims, No Drawings

HYPOGLYCAEMICALLY AND HYPOLIPIDAEMICALLY EFFECTIVE N-SUBSTITUTED CARBOXYLIC ACID AMIDES

The present invention is concerned with new N-substituted carboxylic acid amides and with the preparation thereof.

The new N-substituted carboxylic acid amides according to the present invention are compounds of the general formula:

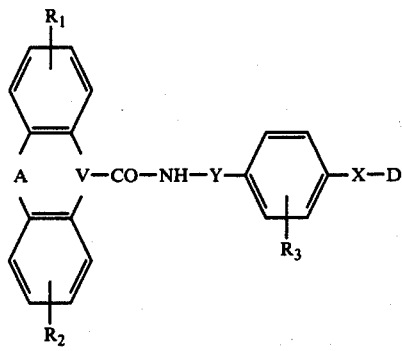

wherein A is a valency bond, an oxygen or a sulphur atom or a methylene, ethylene, vinylene, ethyleneoxa (—$CH_2$—O—) or ethylenethia (—$CH_2$—S—) radical, V is a straight-chained or branched, saturated or unsaturated trivalent hydrocarbon radical containing up to 4 carbon atoms, $R_1$ and $R_2$, which may be the same or different, are hydrogen or halogen atoms, hydroxyl groups or alkyl or alkoxy radicals, $R_3$ is a hydrogen atom, a hydroxyl group or an alkoxy radical, Y is a branched or unbranched alkylene radical containing up to 3 carbon atoms, X is a valency bond or a straight-chained or branched, saturated or unsaturated divalent aliphatic hydrocarbon radical containing up to 6 carbon atoms and D is a hydroxymethyl, formyl, free or esterified carboxyl or N-substituted carbamoyl radical; and the physiologically compatible salts thereof.

The alkyl and alkoxy radicals are, in all cases, straight-chain or branched radicals containing up to 5 carbon atoms, the alkyl radical preferably being a methyl radical and the alkoxy radical preferably being a methoxy to butoxy radical.

The trivalent hydrocarbon radical V is preferably one of the following:

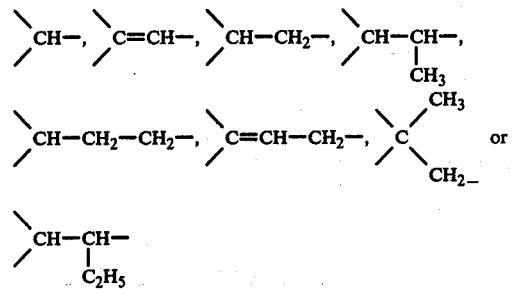

By halogen, there is to be understood a fluorine, chlorine or bromine atom.

The new compounds of general formula (I) and the physiologically compatible salts thereof possess surprisingly marked hypoglycaemic and/or hypolipidaemic properties.

Preferred sub-groups of compounds include those wherein:

A is a valency bond or an oxygen or sulphur atom or a methylene, ethylene, vinylene, ethyleneoxa or ethylenethia radical; and/or $R_3$ is a hydroxyl group or an alkoxy radical containing up to 5 carbon atoms; and/or X is a valency bond or —$CH_2$—$CH_2$—; and/or D is a hydroxymethyl or formyl radical, a carboalkoxy radical wherein the alkoxy radical has up to 4 carbon atoms; or a carbonylamido radical of a naturally occurring amino acid.

The new compounds of general formula (I) according to the present invention can be prepared, for example, by one of the following methods:

(a) reaction of an amine of the general formula:

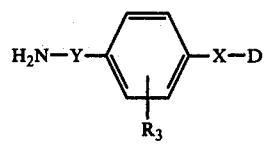

wherein D, Y, X and $R_3$ have the same meanings as above, with a reactive acid derivative of an acid of the general formula T.COOH, wherein T is a tricyclic system of the general formula:

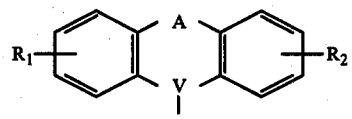

wherein A, V, $R_1$ and $R_2$ have the same meanings as above; or (b) for the case in which D is a carboxyl group, oxidation of a compound of the general formula:

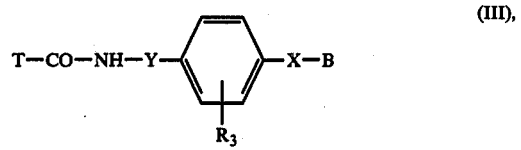

wherein T, Y, $R_3$ and X have the same meanings as above and B is a residue which can be converted into a carboxyl group by oxidation; or (c) for the case in which X is a straight-chain or branched, saturated or unsaturated divalent aliphatic hydrocarbon radical containing up to 6 carbon atoms, reduction of a compound of the general formula:

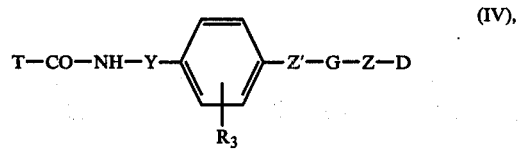

wherein D, T, $R_3$ and Y have the same meanings as above, Z and Z', which can be the same or different, represent valency bonds or a straight-chain or branched, saturated or unsaturated divalent aliphatic hydrocarbon radical containing up to 5 carbon atoms, and G is a —CO— or —CH(L)— radical, L being a halogen atom or a hydroxyl group; or (d) for the case in which X is a straight-chain or branched, saturated or unsaturated divalent aliphatic hydrocarbon radical containing 2 to 6 carbon atoms and D is a carboxyl or formyl group, reaction of a compound of the general formula:

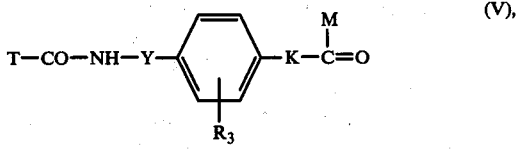

wherein T, R$_3$ and Y have the same meanings as above, M is a hydrogen atom or an alkyl radical containing up to 4 carbon atoms and K is a valency bond or a straight-chain or branched, saturated or unsaturated divalent aliphatic hydrocarbon radical containing up to 4 carbon atoms, with a reactive methylene component of the general formula:

wherein D' is a formyl or a —COOR' radical, R' being a hydrogen or alkali metal atom or a lower alkyl or acyl radical and Q is a hydrogen atom, an alkyl radical containing up to 4 carbon atoms or an activating group, such as a nitrile group or a —COOR' radical or a —PO(OR)$_2$ radical, R is a hydrogen atom or an alkyl radical and wherein R' has the same meaning as above, the unsaturated compound obtained being, if desired, subsequently saponified, decarboxylated or hydrogenated; or (e) for the case in which X is a straight-chain or branched, saturated or unsaturated divalent aliphatic hydrocarbon radical containing up to 6 carbon atoms and D is a carboxyl group, reaction of a derivative of a carboxylic acid of the general formula:

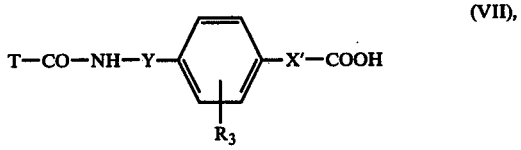

wherein T, R$_3$ and Y have the same meanings as above and X' is a radical which is one methylene group smaller than X, with diazomethane according to the Arndt-Eistert reaction; or (f) for the case in which X is a straight-chain saturated alkylene chain containing up to 4 carbon atoms and D is a carboxyl group, reaction of a ketone of the general formula:

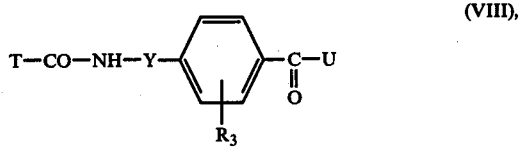

wherein T, R$_3$ and Y have the same meanings as above and U is an alkyl radical containing up to 4 carbon atoms, under the conditions of a possibly modified Willgerodt-Kindler synthesis; or (g) for the case in which X is a straight-chain or branched, saturated or unsaturated divalent aliphatic hydrocarbon radical containing 2 to 6 carbon atoms and D is a carboxyl or formyl group, reaction of a halogen compound of the general formula:

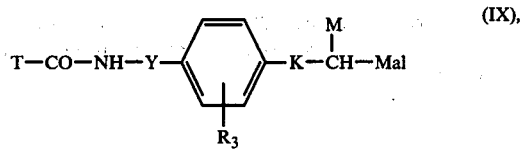

wherein T, R$_3$, Y, K and M have the same meanings as above and Hal is a halogen atom, with a reactive methylene component of the general formula:

wherein D" is a formyl or —COOR$_5$ radical, R$_5$ being a lower alkyl radical, Me is an alkali metal or alkaline earth metal atom, R$_4$ is a hydrogen atom or an alkyl radical containing up to 4 carbon atoms and W is an —OR$_5$ or methyl radical, saponification and possible decarboxylation;

whereafter, if desired, the compound obtained of general formula (I) is converted into a different compound of general formula (I) or an acid derivative obtained of general formula (I) is, if desired, converted into the corresponding free acid or a free acid obtained of general formula (I) is, if desired, esterified or converted into an amide or into a physiologically compatible salt.

In the case of process (a), the reactive derivative of the acid T.COOH is preferably an acid chloride, which can be obtained in the usual manner, for example, by reaction of the carboxylic acid with thionyl chloride. However, equally well, there can also be used the esters, azides, anhydrides or mixed anhydrides thereof. Such reactive intermediates can also be prepared in a one-pot process and immediately further reacted.

The reaction with the intermediate of general formula (II) can be carried out by the Schotten-Baumann reaction. If it is desired to work under anhydrous conditions, then it is preferable to use anhydrous pyridine or some other organic solvent, such as toluene, methylene chloride, acetone or dioxane, with the addition of a tertiary amine, for example triethylamine. However, instead of the free amine compound, the salts thereof can also be used.

As amino components of the general formula (II), there are preferably used, for the case in which D is a possibly esterified carboxyl or an N-substituted carbamoyl radical, the esters, especially the methyl and ethyl esters, nitriles, acid amides or acid anhydrides, which, after the reaction has taken place, can, if desired, be converted by hydrolysis in known manner into the free carboxylic acids or into the desired derivatives thereof.

In the case of process (b) in which D is a carboxyl group, as oxidizable group B in compounds of general formula (III) there are preferably used the hydroxymethyl, aminomethyl, formyl or acetyl radicals or the functional derivatives thereof which can be oxidized with conventional oxidizing agents, for example permanganates or dichromates, or, in the case of the formyl radical, also with atmospheric oxygen or silver oxide or, in the case of the acetyl radical, also with alkali metal hypohalites, the carboxyl group thereby being easily obtained.

The compounds of general formula (III) can be prepared in known manner, especially analogously to process (a), whereby, instead of the acid or derivative thereof of general formula (II), there is used a corresponding compound containing an oxidizable group B. Of course, on the other hand, compounds of general formula (I), wherein D is a carboxyl group, or acid derivatives thereof, for example esters, acid halides and acid amides, can be converted into compounds of general formula (III) by reduction.

The ketones of general formula (IV) used as starting materials in the case of process (c) can be prepared in known manner, especially analogously to process (a), whereby, instead of a compound of general formula (II), there is employed a corresponding derivative containing a reducible residue G.

For the case in which Z is other than a valency bond and D is a carboxyl group or a derivative thereof, the ketocarboxylic acid derivative of general formula (IV) used as starting material in the case of process (c) can also be prepared, for example, by a Claisen ester condensation.

The compounds of general formula (IV), which are used as starting material in process (c), are new and also possess hypoglycaemic and/or hypolipidaemic properties.

The reduction of compounds of general formula (IV) in which G is a keto group, to give compounds of general formula (I), can be carried out, for example, with the help of zinc/hydrochloric acid in the manner of a Clemmensen reduction or with hydrazine/alkali in the manner of a Wolff-Kishner reduction. However, the reduction is preferably carried out catalytically with hydrogen in the presence of a noble metal, for example palladium or platinum. In this case, the preferred solvent is a lower alcohol. However, it is also possible to work in glacial acetic acid to which has been added a trace of sulphuric or perchloric acid or a molar amount of hydrochloric acid. The reaction temperature is preferably from 20° to 60° C. and the hydrogen pressure is preferably between 1 and 10 ats.

Compounds of general formula (IV) in which G is a —CH(OH)— radical can be prepared, for example, by the reduction of the corresponding keto derivatives. The reduction can be carried out catalytically in the presence of a noble metal, for example palladium or platinum. As reducing agent, there can also be used a complex metal hydride, preferably sodium borohydride. In this case, the reaction can be carried out in an alcohol, especially in methanol, or also in an aqueous alkaline medium. From the hydroxy compounds, there can also be prepared the halogen derivatives, using generally known methods. The reduction to compounds of general formula (I) can also be carried out in known manner, for example, according to the above-described conditions (G is a keto group).

The reaction according to process (d) is carried out under the well-known conditions of the Perkin reaction or of the Knoevenagel reaction. The derivatives prepared according to the Cope variation or from the carbonyl compounds with 2-phosphonoalkaneic acid trialkyl esters in the presence of alcoholates, are subsequently saponified, possibly with decarboxylation.

By lower alkyl in the case of substituents R and R', there is to be understood an alkyl radical containing up to 5 carbon atoms, especially a methyl or ethyl radical. The olefinic derivatives thus prepared can be hydrogenated to give the saturated compounds, for example catalytically with hydrogen in the presence of palladium or platinum.

The process (e) involves the Arndt-Eistert method in which a derivative, especially a chloride, of a carboxylic acid of general formula (VII) is converted into a diazoketone with diazomethane. By the action of ultraviolet light, heat or a catalyst, for example silver oxide, the diazoketone is converted into a carboxylic acid derivative of general formula (I).

The ketones of general formula (VIII) used in the case of process (f) can be prepared by known processes, especially analogously to process (a), whereby, instead of the acid or a derivative thereof of general formula (II), there is employed the corresponding intermediate containing a —CO—U group. This intermediate can easily be prepared by acylation by the Friedel-Crafts method. The thiomorpholide obtained in the case of the Willgerodt-Kindler synthesis is saponified in an alkaline or acidic medium.

Instead of sulphur and a secondary amine, for the simultaneous reduction of the carbonyl group to a methylene radical and oxidation of a methyl radical to a carboxyl radical, there can also be used a thallium (III) salt, preferably thallium (III) nitrate, and perchloric acid.

The reaction according to process (g) is carried out according to the methods known for the alkylation of $\beta$-dicarbonyl compounds. The subsequent saponification of the $\beta$-diketo compound is preferably carried out with an alcoholate under ester splitting conditions. By a lower alkyl substituent $R_5$, there is to be understood an alkyl radical containing up to 5 carbon atoms, preferably a methyl or ethyl radical.

For the case in which $R_1$, $R_2$ and/or $R_3$ signifies a hydroxyl group, these substituents must be protected before the reaction by means of appropriate groups which can easily be split off.

The subsequent conversion of a compound of general formula (I) into another compound of general formula (I) can be carried out, for example, by alkylation of a hydroxyl group in known manner by reaction of the alkali metal phenolate with a dialkyl sulphate or alkyl halide.

In the same way, from alkoxy compounds of general formula (I), there can be obtained hydroxyl-substituted compounds of general formula (I) by known methods of ether splitting, for example with the use of hydroiodic acid or of a Lewis acid.

Furthermore, compounds of general formula (I) containing an olefinic double bond can be converted into the corresponding saturated compounds of general formula (I) in known manner by hydrogenation with hydrogen in the presence of a catalyst.

Carboxylic acids or the derivatives thereof of general formula (I) can be converted by known reduction methods into the corresponding aldehydes or alcohols of general formula (I).

The esters obtained as intermediates in the case of the above-mentioned processes can be isolated and, if desired, saponified directly to give the corresponding carboxylic acids. On the other hand, when carboxylic acids are obtained, they can be reacted in known manner to give the corresponding desired esters.

Saponification of the esters, nitriles, amides and the like are preferably carried out in an alkaline medium.

For a possibly desired esterification of the carboxyl group, there can, in principle, be used all alcohols. The lower monohydroxy alcohols are preferred, such as methanol, ethanol or propanol, as well as polyhydroxy alcohols, such as glycol, or alcohols with other functional groups, such as ethanolamine or glycol ethers.

Compounds of general formula (I), in which D is an N-substituted carbamoyl group, can be prepared in known manner from the free carboxylic acids or from the reactive derivatives thereof by reaction with amines. As amine component, there can be used, for example, an alkylamine, dialkylamine or the like. However, it is preferred to use amine acids, such as p-aminobenzoic acid, anthranilic acid, phenylalanine, alanine, or β-alanine.

The preferred physiologically compatible salts include, in particular, the alkali metal, alkaline earth metal and ammonium salts, as well as salts with blood sugar-lowering effective basic compounds, preferably biguanides. These salts can be prepared in known manner, for example, by reaction with appropriate free bases or carbonates.

As blood sugar-lowering and/or anti-hyperlipidaemic compositions according to the present invention, there can be used all the forms of administration conventionally employed for the oral or parenteral routes, for example, tablets, capsules, dragees, syrups, solutions, suspensions, drops, suppositories and the like. For this purpose, the active material is mixed with solid or liquid carriers or diluents, followed by subsequently bringing into the desired form. Solid carrier materials include, for example, starch, lactose, mannitol, methyl cellulose, talc, highly-dispersed silicic acid, high molecular weight fatty acids (such as stearic acid), gelatin, agar-agar, calcium phosphate, magnesium stearate, animal and vegetable fats and solid high molecular weight polymers (such as polyethylene glycols). Compositions suitable for oral administration can, if desired, contain flavoring and sweetening agents. As injection medium, it is preferred to use water which contains the additives conventional in the case of injection solutions, such as stabilising agents, solubilising agents and/or buffers. Additives of this type include, for example, acetate or tartrate buffers, ethanol, complex-forming agents (such as ethylenediamine-tetraacetic acid and the non-toxic salts thereof) or high molecular weight polymers (such as liquid polyethylene oxide) for viscosity regulation.

Preferred compounds according to the present invention are, in addition to those mentioned in the specific examples, are also the following compounds:
3-{4-[2-(3-{fluorenyl-(9)}-propionamido)-ethyl]-phenyl}-propionic acid;
4-{2-[3-(fluorenylidene-(9))-propionamido]-ethyl}-benzoic acid;
3-{4-[2-(6,11-dihydrodibenzo[b,e]oxepin-11-carboxamido)-ethyl]-phenyl}-propionic acid;
3-{4-[2-(fluorenyl-(9)-acetamido)-ethyl]-phenyl}-2,2-dimethylpropionic acid; and
3-{4-[2-(4,5-dimethoxyfluorenyl-(9)-acetamido)-ethyl]-phenyl}-propionic acid.

The following examples are given for the purpose of illustrating the present invention:

EXAMPLE 1

3-{4-[2-(Xanthene-9-carboxamido)-ethyl]-phenyl}-propionic acid.

A solution of 3.0 g. xanthene-9-carboxylic acid chloride (prepared from xanthene-9-carboxylic acid and thionyl chloride) in 15 ml. methylene chloride is added at 0° C. to 3.2 g. ethyl 3-[4-(2-aminoethyl)-phenyl]-propionate hydrochloride (m.p. 165°–167° C.) in 24.5 ml. 1N aqueous sodium hydroxide solution. The reaction mixture is stirred for 0.5 hours while cooling with ice and then for 2 hours at ambient temperature, whereafter the two phases are separated and the aqueous phase is shaken out with methylene chloride. The combined organic phases are successively washed with dilute aqueous sodium hydroxide solution and dilute hydrochloric acid, then dried and the methylene chloride evaporated off. The residue is crystallized from ethanol. There are obtained 4.2 g. (80% of theory) ethyl 3-{4-[2-(xanthene-9-carboxamido)-ethyl]-phenyl}-propionate; m.p. 144°–147° C.

4.0 g. ethyl 3-{4-[2-(xanthene-9-carboxamido)-ethyl]-phenyl}-propionate are heated under reflux for 2 hours with a solution of 1.6 g. sodium hydroxide in 40 ml. ethanol. The reaction mixture is then cooled and sodium 3-{4-[2-(xanthene-9-carboxamido)-ethyl]-phenyl}-propionate thereby precipitates out. It is filtered off with suction, washed with a little ethanol, dissolved in water and the solution acidified. The free carboxylic acid is filtered off with suction and recrystallized from ethanol. The yield is 3.0 g. (80.5% of theory); m.p. 180°–183° C.

The following compounds are obtained in an analogous manner:

1. by the reaction of ethyl 3-[4-(2-aminoethyl)-phenyl]-propionate hydrochloride with the appropriate carboxylic acid chlorides:
(a) ethyl 3-{4-[2-(5H-dibenzo[a,d]cycloheptenyl-(5)-acetamido)-ethyl]-phenyl}-propionate;
m.p. 105°–107° C. (recrystallized from 80% isopropanol) and from this, by saponification
3-{4-[2-(dibenzo[a,d]cycloheptenyl-(5)-acetamido)-ethyl]-phenyl}-propionic acid;
m.p. 174°–177° C. (recrystallized from 50% methanol);
(b) ethyl 3-{4-[2-(6,11-dihydrodibenz[b,e]oxepinyl-(11)-acetamido)-ethyl]-phenyl}-propionate;
m.p. 88°–89° C. (recrystallized from 80% isopropanol) and from this, by saponification
3-{4-[2-(6,11-dihydrodibenz[b,e]oxepinyl-(11)-acetamido)-ethyl]-phenyl}-propionic acid;
m.p. 124°–125° C. (recrystallized from 80% isopropanol);
(c) ethyl 3-{4-[2-(3-methylfluorenyl-(9)-acetamido)-ethyl]-phenyl}-propionate;
m.p. 90°–92° C. (recrystallized from methylene chloride) and from this, by saponification
3-{4-[2-(3-methylfluorenyl-(9)-acetamido)-ethyl]-phenyl}-propionic acid;
m.p. 184°–187° C. (purified via the sodium salt);
(d) ethyl 3-{4-[2-(fluorenylidene-(9)-acetamido)-ethyl]-phenyl}-propionate;
m.p. 130° C. (recrystallized from methylene chloride);
and from this, by saponification
3-{4-[2-(fluorenylidene-(9)-acetamido)-ethyl]-phenyl}-propionic acid;
m.p. 203°–204° C. (recrystallized from ethanol);

(e) ethyl 3-{4-[2-(fluorenyl-(9)-acetamido)-ethyl]-phenyl}-propionate;
  m.p. 122°–124° C. (recrystallized from methylene chloride) and from this, by saponification
3-{4-[2-(fluorenyl-(9)-acetamido)-ethyl]-phenyl}-propionic acid;
  m.p. 218°–219° C. (recrystallized from ethyl acetate);
(f) ethyl 3-{4-[2-(2-methyl-6,11-dihydrodibenze[b,e]oxepinyl-(11)-acetamido)-ethyl]-phenyl}-propionate (oily);
and from this, by saponification
3-{4-[2-(2-methyl-6,11-dihydrodibenzo[b,e]oxepinyl-(11)-acetamido)-ethyl]-phenyl}-propionic acid;
  m.p. 174°–175° C. (recrystallized from ethanol);
(g) ethyl 3-{4-[2-(9,10-dihydroanthryl-(9)-acetamido)-ethyl]-phenyl}-propionate;
  m.p. 138°–139° C. (recrystallized from ethanol);
and from this, by saponification
3-{4-[2-(9,10-dihydroanthryl-(9)-acetamido)-ethyl]-phenyl}-propionic acid;
  m.p. 198°–200° C. (recrystallized from ethanol);
(h) ethyl 3-{4-[2-(2-{fluorenyl-(9)}-propionamido)-ethyl]-phenyl}-propionate (oily);
and from this, by saponification
3-{4-[2-(2-{fluorenyl-(9)}-propionamido)-ethyl]-phenyl}-propionic acid;
  m.p. 139°–142° C. (recrystallized from isopropanol + 10% water).

2. by the reaction of ethyl 4-(2-aminoethyl)-benzoate hydrochloride (m.p. 195°–200° C.) with the appropriate carboxylic acid chlorides;
(a) ethyl 4-[2-(xanthenyl-(9)-acetamido)-ethyl]-benzoate;
  m.p. 160°–163° C. (recrystallized from methylene chloride);
and from this, by saponification
4-[2-(xanthenyl-(9)-acetamido)-ethyl]-benzoic acid;
  m.p. 256°–258° C. (recrystallized from ethanol);
(b) ethyl 4-[2-(fluorene-9-carboxamido)-ethyl]-benzoate;
  m.p. 188°–191° C. (recrystallized from methylene chloride);
and from this, by saponification
4-[2-(fluorene-9-carboxamido)-ethyl]-benzoic acid;
  m.p. 250° C. (purified via the sodium salt);
(c) ethyl 4-[2-(6,11-dihydrodibenzo[b,e]oxepinyl-(11)-acetamido)-ethyl]-benzoate (oily);
and from this, by saponification
4-[2-(6,11-dihydrodibenz[b,e]oxepinyl-(11)-acetamido)-ethyl]-benzoic acid;
  m.p. 178°–182° C. (recrystallized from ethyl acetate);
(d) ethyl 4-[2-(10,11-dihydro-5H-dibenzo[a,d]cycloheptenyl-(5)-acetamido)-ethyl]-benzoate;
  m.p. 127°–130° C. (recrystallized from diethyl ether);
and from this, by saponification
4-[2-(10,11-dihydro-5H-dibenzo[a,d]cycloheptenyl-(5)-acetamido)-ethyl]-benzoic acid;
  m.p. 203°–206° C. (recrystallized from ethanol/water);
(e) ethyl 4-[2-(2,6-dimethylfluorenyl-(9)-acetamido)-ethyl]-benzoate;
  m.p. 145°–148° C. (recrystallized from toluene);
and from this, by saponification
4-[2-(2,6-dimethylfluorenyl-(9)-acetamido)-ethyl]-benzoic acid;
  m.p. 224°–225° C. (recrystallized from isopropanol);
(f) ethyl 4-[2-(9,10-dihydroanthryl-(9)-acetamido)-ethyl]-benzoate;
  m.p. 149°–152° C. (recrystallized from ethanol);
and from this, by saponification
4-[2-(9,10-dihydroanthryl-(9)-acetamido)-ethyl]-benzoic acid;
  m.p. 239°–241° C. (recrystallized from ethanol).

3. by the reaction of ethyl 4-(2-aminoethyl)-phenylacetate hydrochloride (m.p. 177°–178° C.) with fluorenyl-(9)-acetyl chloride:
ethyl 4-[2-(fluorenyl-(9)-acetamido)-ethyl]-phenyl-acetate;
  m.p. 143°–146° C. (recrystallized from methylene chloride);
and from this, by saponification
4-[2-(fluorenyl-(9)-acetamido)-ethyl]-phenylacetic acid;
  m.p. 212°–214° C. (recrystallized from isopropanol);

4. by the reaction of ethyl 2-[4-(2-aminoethyl)-phenyl]-butyrate hydrochloride (oily) with fluorenyl-(9)-acetyl chloride:
ethyl 2-{4-[2-(fluorenyl-(9)-acetamido)-ethyl]-phenyl}-butyrate (wax-like);
and from this, by saponification
2-{4-[2-(fluorenyl-(9)-acetamido)-ethyl]-phenyl}-butyric acid;
  m.p. 88°–90° C. (recrystallized from xylene);

5. by the reaction of ethyl 3-[4-(aminomethyl)-phenyl]-propionate hydrochloride (m.p. 192°–193° C.) with fluorenyl-(9)-acetyl chloride:
ethyl 3-[4-(fluorenyl-(9)-acetamido-methyl)-phenyl]-propionate;
  m.p. 155°–156° C. (recrystallized from isopropanol);
and from this, by saponification
3-[4-(fluorenyl-(9)-acetamido-methyl)-phenyl]-propionic acid;
  m.p. 163°–165° C. (purified via the potassium salt);

6. by the reaction of ethyl 3-[4-(2-aminopropyl)-phenyl]-propionate hydrochloride (m.p. 115°–117° C.) with fluorenyl-(9)-acetyl chloride:
ethyl 3-{4-[2-(fluorenyl-(9)-acetamido)-propyl]-phenyl}-propionate (oily);
and from this, by saponification
3-{4-[2-(fluorenyl-(9)-acetamido)-propyl]-phenyl}-propionic acid;
  m.p. 173°–174° C. (recrystallized from toluene);

7. by the reaction of ethyl 4-(2-aminoethyl)-cinnamate hydrochloride (m.p. 218°–220° C.) with fluorenyl-(9)-acetyl chloride:
ethyl 4-[2-(fluorenyl-(9)-acetamido)-ethyl]-cinnamate;
  m.p. 160°–162° C. (recrystallized from methylene chloride);
and from this, by saponification
4-[2-(fluorenyl-(9)-acetamido)-ethyl]-cinnamic acid;
  m.p. 275°–276° C. (recrystallized from glacial acetic acid);

8. by the reaction of ethyl α-methyl-4-(2-aminoethyl)-cinnamate hydrochloride (m.p. 270° C.) with fluorenyl-(9)-acetyl chloride:
ethyl α-methyl-4-[2-(fluorenyl-(9)-acetamido)-ethyl]-cinnamate;
  m.p. 157°–159° C. (recrystallized from xylene);
and from this, by saponification
α-methyl-4-[2-(fluorenyl-(9)-acetamido)-ethyl]cinnamic acid;
  m.p. 223°–226° C. (recrystallized from 70% methanol);

9. by the reaction of ethyl 2-methoxy-4-(2-aminoethyl)-benzoate hydrochloride (m.p. 86°–88° C.)
  (a) with fluorenyl-(9)-acetyl chloride:

ethyl 2-methoxy-4-[2-(fluorenyl-(9)-acetamido)-ethyl]-benzoate (oil);
and from this, by saponification
2-methoxy-4-[2-(fluorenyl-(9)-acetamido)-ethyl]-benzoic acid;
m.p. 164°-168° C. (recrystallized from isopropanol);
(b) with 3-methoxy-fluorenyl-(9)-acetyl chloride:
ethyl 2-methoxy-4-[2-(3-methoxy-fluorenyl-(9)-acetamido)-ethyl]-benzoate (oily);
and from this, by saponification
2-methoxy-4-[2-(3-methoxy-fluorenyl-(9)-acetamido)-ethyl]-benzoic acid;
m.p. 143°-147° C. (recrystallized from toluene);
10. by reaction of ethyl 5-[4-(2-aminoethyl)-phenyl]-valerate hydrochloride (m.p. 148°-152° C.) with fluorenyl-(9)-acetyl chloride:
ethyl 5-{4-[2-(fluorenyl-(9)-acetamido)-ethyl]-phenyl}-valerate;
m.p. 88°-92° C. (recrystallized from isopropanol);
and from this, by saponification
5-{4-[2-(fluorenyl-(9)-acetamido)-ethyl]-phenyl}-valeric acid;
m.p. 158°-161° C. (recrystallized from ethyl acetate);
11. by the reaction of ethyl 2-[4-(2-aminoethyl)-phenyl]-propionate hydrochloride (m.p. 124°-125° C.) with fluorenyl-(9)-acetyl chloride:
ethyl 2-{4-[2-fluorenyl-(9)-acetamido)-ethyl]-phenyl}-propionate (oily);
and from this, by saponification
2-{4-[2-(fluorenyl-(9)-acetamido)-ethyl]-phenyl}-propionic acid;
m.p. 127°-128° C. (sinters at 75° C.) (recrystallized from isopropanol).
12. by the reaction with ethyl 7-[4-(2-aminoethyl)-phenyl[-heptanoate hydrochloride (m.p. 135°-138° C.) with fluorenyl-(9)-acetyl chloride:
ethyl 7-{4-[2-(fluorenyl-(9)-acetamido)-ethyl]-phenyl}-heptanoate (oily);
and from this, by saponification
7-{4-[2-(fluorenyl-(9)-acetamido)-ethyl]-phenyl}-heptanoic acid;
m.p. 176°-179° C. (recrystallized from ethanol).

EXAMPLE 2

4-{2-[3-(Fluorenyl-(9))-propionamido]-ethyl}-benzoic acid.

A solution of 3-(fluorenyl-(9))-propionyl chloride (prepared from 1.7 g. 3-(fluorenyl-(9))-propionic acid and thionyl chloride) and 12 ml. methylene chloride is added dropwise at 0° C. to 1.5 g. 4-(2-aminoethyl)-benzoic acid hydrochloride in 25.2 ml. 1N-aqueous sodium hydroxide solution. The reaction mixture is stirred for 0.5 hours while cooling with ice and then for 2 hours at ambient temperature. The phases are then separated, the aqueous alkaline phase is again washed with methylene chloride and the desired free carboxylic acid is precipitated out by acidification with dilute hydrochloric acid. It is filtered off with suction and recrystallized from ethanol. The yield is 1.6 g. (58.1% of theory); m.p. 219°-221° C.

(a) In an analogous manner, by the reaction of 4-(2-aminoethyl)-benzoic acid hydrochloride with fluorenyl-(9)-acetyl chloride, there is obtained 4-[2-(fluorenyl-(9)-acetamido)-ethyl]-benzoic acid; m.p. 248°-250° C. (recrystallized from ethanol).

EXAMPLE 3

3-{4-[2-(Thioxanthenyl-(9)-acetamido)-ethyl]-phenyl}-propionic acid.

4.0 g. thioxanthenyl-(9)-acetic acid and 4.0 g. ethyl 3-[4-(2-aminoethyl)-phenyl]-propionate hydrochloride are suspended in 20 ml. methylene chloride. While cooling to −15° C., there is added thereto first 1.5 ml. phosphorus oxychloride, followed by the slow addition, while stirring, of 6.4 ml. triethylamine. The reaction mixture is then stirred for 1 hour at −10° C. and subsequently for 1 hour at ambient temperature. The methylene chloride phase is then separated off and shaken out with 2N hydrochloric acid and thereafter with 2N aqueous sodium hydroxide solution. The organic phase is dried and evaporated. The residue is ethyl 3-{4-[2-(thioxanthenyl-(9)-acetamido)-ethyl]-phenyl}-propionate, the yield being 6.0 g. (83.4% of theory); m.p. 122°-127° C.

6 g. ethyl 3-{4-[2-(thioxanthenyl-(9)-acetamido)-ethyl]-phenyl}-propionate are boiled under reflux for 2 hours in a solution of 3 g. potassium hydroxide in 50 ml. ethanol. The reaction mixture is then cooled and the precipitated potassium salt is filtered off with suction, washed with ethanol and dissolved in water. By acidification with dilute hydrochloric acid, there is obtained the desired free carboxylic acid, which is recrystallized from ethylene chloride; yield 3.3 g. (58.2% of theory); m.p. 188°-189° C.

In an analogous manner, there is obtained:
1. by the reaction of ethyl 4-(2-aminoethyl)-benzoate hydrochloride with the appropriate carboxylic acids, the following compounds:
(a) ethyl 4-[2-(6,11-dihydrodibenzo[b,e]thiepinylidene-(11)-acetamido)-ethyl]-benzoate (oily);
and from this, by saponification
4-[2-(6,11-dihydrodibenzo[b,e]thiepinylidene-(11)-acetamido)-ethyl]-benzoic acid;
m.p. 187°-189° C. (recrystallized from 2-nitropropane);
(b) ethyl 4-{2-[3-(6,11-dihydrodibenzo[b,e]oxepinyl-(11)-propionamido]-ethyl}-benzoate (oily);
and from this, by saponification
4-{2-[3-(6,11-dihydrodibenzo[b,e]oxepinyl-(11)-propionamido]-ethyl}-benzoic acid;
m.p. 55° C. (after dissolving in dilute aqueous sodium carbonate solution, treating with active charcoal and precipitating with dilute hydrochloric acid);
2. by the reaction with ethyl 3-[4-(2-aminoethyl)-phenyl]-propionate hydrochloride with the appropriate carboxylic acid, the following compounds:
(a) ethyl 3-{4-[2-(9,10-dihydroanthracene-9-carboxamido)-ethyl]-phenyl}-propionate (oily);
and from this, by saponification
3-{4-[2-(9,10-dihydroanthracene-9-carboxamido)-ethyl]-phenyl}-propionic acid;
m.p. 143°-149° C. (recrystallized from 80% ethanol);
(b) ethyl 3-{4-[2-(fluorenyl-(9)-carboxamido)-ethyl]-phenyl}-propionate;
m.p. 138°-140° C. (recrystallized from 80% ethanol);
and from this, by saponification
3-{4-[2-(fluorenyl-(9)-carboxamido)-ethyl]-phenyl}-propionic acid;
m.p. 205°-206° C. (recrystallized from isopropanol);
(c) ethyl 3-{4-[2-(3-methoxy-fluorenyl-(9)-acetamido)-ethyl]-phenyl}-propionate (oil);
and from this, by saponification 3-{4-[2-(3-methoxy-fluorenyl-(9)-acetamido)-ethyl]-phenyl}-propionic acid;
m.p. 187°-188° C. (recrystallized from ethanol);
(d) ethyl 3-{4-{2-[3-(fluorenylidene-(9))-propionamido]-ethyl-}phenyl}-propionate (oil);
and from this, by saponification
3-{4-{2-[3-(fluorenylidene-(9))-propionamido]-ethyl}-phenyl}-propionic acid;
m.p. 236°-238° C. (recrystallized from 80% isopropanol);
(e) ethyl 3-{4-[2-(6,11-dihydrodibenzo[b,e]thiepinyl-(11)-acetamido)-ethyl]-phenyl}-propionate (oil);
and from this, by saponification
3-{4-[2-(6,11-dihydrodibenzo[b,e]thiepinyl-(11)-acetamido)-ethyl]-phenyl}-propionic acid;
m.p. 154°-155° C. (recrystallized from toluene);
3. by the reaction of ethyl 4-(2-aminoethyl)-2-methoxybenzoate hydrochloride with [1-methoxy-fluorenyl-(9)]-acetic acid:
ethyl 2-methoxy-4-[2-(1-methoxy-fluorenyl-(9)-acetamido)-ethyl]-benzoate (oil);
and from this, by saponification
2-methoxy-4-[2-(1-methoxy-fluorenyl-(9)-acetamido)-ethyl]-benzoic acid;
m.p. 155°-157° C. (recrystallized from isopropanol).

EXAMPLE 4

4-[2-(2-Methoxy-6,11-dihydrodibenzo[b,e]oxepinylidene-(11)-acetamido)-ethyl]-benzoic acid.

A solution of 0.75 g. phosphorus trichloride in 10 ml. anhydrous pyridine is added dropwise at 0° C. to 2.5 g. ethyl 4-(2-aminoethyl)-benzoate hydrochloride in 20 ml. anhydrous pyridine. The solution is stirred at 0° C. for 15 minutes and at 20° C. for 30 minutes, whereafter 2.82 g. 2-methoxy-6,11-dihydrodibenz[b,e]oxepinylidene-(11)-acetic acid are added thereto. The reaction mixture is stirred overnight, then poured on to ice-cold hydrochloric acid and extracted several times with methylene chloride. The organic phase is neutralized with an aqueous solution of sodium bicarbonate, dried and evaporated. There are obtained 3.4 g. of the ester in the form of an oil. These 3.4 g. of ester are saponified with 25 ml. 2N aqueous sodium hydroxide solution and 25 ml. ethanol for 30 minutes on a water-bath. The ethanol is then stripped off and the aqueous solution is extracted with methylene chloride and acidified. The oil which separates is taken up in methylene chloride, dried and completely evaporated. The residue is recrystallized from ethyl acetate. Yield of the desired carboxylic acid 2.1 g. (49% of theory); m.p. 191°-193° C.

(a) In an analogous manner, there is obtained, by the reaction of ethyl 4-(2-aminoethyl)-benzoate hydrochloride with 6,11-dihydrodibenz[b,e]oxepinylidene-(11)-acetic acid, ethyl 4-[2-(6,11-dihydrodibenz[b,e]oxepinylidene-(11)-acetamido)-ethyl]-benzoate (oil) and from this, by saponification, 4-[2-(6,11-dihydrodibenz[b,e]oxepinylidene-(11)-acetamido)-ethyl]-benzoic acid; m.p. 247°-250° C. (recrystallized from 50% methanol).

EXAMPLE 5

3-{4-[2-(Fluorenyl-(9)-acetamido)-ethyl]-phenyl}-2-methylpropionic acid.

5.3 g. α-methyl-4-[2-(fluorenyl-(9)-acetamido)-ethyl]-cinnamic acid are hydrogenated at atmospheric pressure in the presence of palladium-charcoal in 100 ml. glacial acetic acid and 2 ml. water. After the take up of 1 mole hydrogen per mole of starting material, the reaction is ended. After filtering off the catalyst with suction, the filtrate is evaporated and the residue is mixed with water. The precipitated 3-{4-[2-(fluorenyl-(9)-acetamido)-ethyl]-phenyl}-2-methylpropionic acid is filtered off with suction and then washed with water. The product thus obtained is pure. Yield 4.8 g. (90% of theory); m.p. 147°-150° C.

In an analogous manner, there are obtained:
(a) from 4-[2-(fluorenyl-(9)-acetamido)-ethyl]-cinnamic acid:
3-{4-[2-(fluorenyl-(9)-acetamido)-ethyl]-phenyl}-propionic acid;
m.p. 218°-219° C. (recrystallized from ethyl acetate);
(b) from 3-{4-[2-(fluorenylidene-(9)-acetamido)-ethyl]-phenyl}-propionic acid, again
3-{4-[2-(fluorenyl-(9)-acetamido)-ethyl]-phenyl}-propionic acid;
m.p. 218°-219° C. (recrystallized from ethyl acetate).

EXAMPLE 6

4-[2-(Fluorenyl-(9)-acetamido)-ethyl]-cinnamic acid.

A mixture of 3.6 ml. 30% sodium methylate solution and 3.6 ml. methanol is added dropwise, with ice cooling, to 4.2 g. 4-[2-(fluorenyl-(9)-acetamido)-ethyl]-benzaldehyde (m.p. 140°-143° C.) and 4.0 g. triethyl phosphonoacetate in 24 ml. anhydrous dimethyl formamide. The reaction mixture is then stirred for 2 hours at ambient temperature, stirred with ice and water and then adjusted to pH 6 with acetic acid. The ethyl 4-[2-(fluorenyl-(9)-acetamido)-ethyl]-cinnamate formed is filtered off with suction and washed with water. Yield 3.6 g. (70% of theory); m.p. 162°-165° C.

This ester (3.6 g.) is heated under reflux for 2 hours with 2.5 g. potassium hydroxide in 35 ml. ethanol. After cooling, the precipitated potassium salt is filtered off with suction, washed with ethanol and dissolved in water. This solution is treated with active charcoal and thereafter acidified with dilute hydrochloric acid. The desired free carboxylic acid is filtered off with suction and recrystallized from glacial acetic acid. Yield 2.2 g. (65% of theory); m.p. 275°-276° C.

In an analogous manner, there is obtained, by the use of triethyl 2-phosphonopropionate (b.p. 152°-156° C./15 mm.Hg.), ethyl α-methyl-4-[2-(fluorenyl-(9)-acetamido)-ethyl]-cinnamate; m.p. 157°-159° C. (recrystallized from xylene) and from this, by saponification, α-methyl-4-[2-(fluorenyl-(9)-acetamido)-ethyl]-cinnamic acid; m.p. 223°-226° C. (recrystallized from 70% methanol).

EXAMPLE 7

4-[2-(Fluorenyl-(9)-acetamido)-ethyl]-benzoic acid.

4.0 g. sodium dichromate dihydrate are added to a solution of 3.6 g. 4-[2-(fluorenyl-(9)-acetamido)-ethyl]-benzyl alcohol (m.p. 176°-178° C.) in 50 ml. glacial acetic acid and the reaction mixture is stirred for 8 hours at 50° C. The glacial acetic acid is distilled off on a rotary evaporator, the residue is taken up in water and dilute aqueous sodium hydroxide solution and a small amount of unreacted starting material is removed by shaking out with ethyl acetate. The solution is then acidified with dilute hydrochloric acid and the desired free carboxylic acid is thus obtained. After recrystallization from ethanol, the yield is 2.1 g. (56% of theory); m.p. 248°-250° C.

In an analogous manner, with the use of 4-[2-(fluorenyl-(9)-acetamido)-ethyl]-benzaldehyde (m.p.

140°–143° C.) as starting material, there is again obtained 4-[2-(fluorenyl-(9)-acetamido)-ethyl]-benzoic acid.

EXAMPLE 8

(1-Phenethyl-biguanide)-3-{4-[2-(fluorenyl-(9)-acetamido)-ethyl]-phenyl}-propionate.

4.0 g. 3-{4-[2-(Fluorenyl-(9)-acetamido)-ethyl]-phenyl}-propionic acid are dissolved in 100 ml. 0.1N aqueous sodium hydroxide solution. At the same time, there is prepared a solution of 2.42 g. 1-phenethyl biguanide hydrochloride in 40 ml. water. Both solutions are mixed together at ambient temperature and the desired salt thereby precipitates out. After 1 hour, the product is filtered off with suction, washed several times with water and dried in a vacuum drying cabinet at 70° C. There are obtained 2.1 g. (35% of theory) (1-phenethyl-biguanide)-3-{4-[2-(fluorenyl-(9)-acetamido)-ethyl]-phenyl}-propionate; m.p. 104°–106° C. A further quantity of product can be obtained by evaporation of the mother liquor.

EXAMPLE 9

In a manner analogous to that described in Example 1, there are obtained:

1. by the reaction of ethyl 3-[4-(2-aminoethyl)-phenyl]-propionate hydrochloride (a) with the acid chloride prepared from 2-chloro-fluorenyl-(9)-acetic acid (m.p. 95°–98° C.)
   ethyl 3-{4-[2-(2-chlorofluorenyl-(9)-acetamido)-ethyl]-phenyl}-propionate;
   m.p. 84°–86° C. (recrystallized from methylene chloride);
   and from this, by saponification
   3-{4-[2-(2-chlorofluorenyl-(9)-acetamido)-ethyl]-phenyl}-propionic acid;
   m.p. 219°–222° C. (recrystallized from ethanol);

(b) with the acid chloride prepared from 2-[fluorenyl-(9)]-butyric acid (m.p. 119°–121° C.)
   ethyl 3-{4-[2-(2-[fluorenyl-(9)]-butyramido)-ethyl]-phenyl}-propionate;
   m.p. 122°–125° C. (recrystallized from ethanol);
   and from this, by saponification
   3-{4-[2-(2-[fluorenyl-(9)]-butyramido)-ethyl]-phenyl}-propionic acid;
   m.p. 165°–167° C. (recrystallized from ethyl acetate);

(c) with the acid chloride prepared from 9-methyl-fluorenyl-(9)-acetic acid (m.p. 172°–174° C.)
   ethyl 3-{4-[2-(9-methyl-fluorenyl-(9)-acetamido)-ethyl]-phenyl}-propionate (oily)
   and from this, by saponification
   3-{4-[2-(9-methyl-fluorenyl-(9)-acetamido)-ethyl]-phenyl}-propionic acid;
   m.p. 96°–98° C. (purified via the sodium salt);

(d) with the acid chloride prepared from 3-chloro-6-methyl-fluorenyl-(9)-acetic acid (m.p. 110°–112° C.)
   ethyl 3-{4-[2-(3-chloro-6-methyl-fluorenyl-(9)-acetamido)-ethyl]-phenyl}-propionate (oily)
   and from this, by saponification
   3-{4-[2-(3-chloro-6-methyl-fluorenyl-(9)-acetamido)-ethyl]-phenyl}-propionic acid;
   m.p. 225°–227° C. (recrystallized from ethylene chloride);

(e) with the acid chloride prepared from 2-[6,11-dihydrodibenz[b,e]oxepinyl-(11)]-propionic acid
   ethyl 3-{4-[2-(2-{6,11-dihydrodibenz[b,e]oxepinyl-(11)}-propionamido)-ethyl]-phenyl}-propionate (oily);
   and from this, by saponification
   3-{4-[2-(2-{6,11-dihydrodibenz[b,e]oxepinyl-(11)}-propionamido)-ethyl]-phenyl}-propionic acid;
   m.p. 168°–170° C. (recrystallized from acetone);

2. by the reaction of ethyl 3-(2-aminoethyl)-benzoate hydrochloride with 2-[fluorenyl-(9)]-propionyl chloride
   ethyl 4-{2-(2-[fluorenyl-(9)]-propionamido)-ethyl}-benzoate;
   m.p. 96°–97° C. (recrystallized from methylene chloride);
   and from this, by saponification
   4-{2-(2-[fluorenyl-(9)]-propionamido)-ethyl}-benzoic acid;
   m.p. 195°–197° C. (recrystallized from isopropanol);

3. by the reaction of ethyl 2-methoxy-4-(2-aminoethyl)-benzoate hydrochloride with 2-[fluorenyl-(9)]-propionyl chloride
   ethyl 4-{2-(2-[fluorenyl-(9)]-propionamido)-ethyl}-2-methoxy-benzoate (oily)
   and from this, by saponification
   4-{2-(2-[fluorenyl-(9)]-propionamido)-ethyl}-2-methoxybenzoic acid;
   m.p. 91°–93° C. (purified via the sodium salt);

4. by the reaction of ethyl 3-[4-(2-aminoethyl)-2-butoxyphenyl]-propionate hydrochloride (oily) with fluorenyl-(9)-acetyl chloride
   ethyl 3-{2-butoxy-4-[2-(fluorenyl-(9)-acetamido)-ethyl]-phenyl}-propionate;
   m.p. 118°–122° C. (recrystallized from isooctane);
   and from this, by saponification
   3-{2-butoxy-4-[2-(fluorenyl-(9)-acetamido)-ethyl]-phenyl}-propionic acid;
   m.p. 151°–154° C. (recrystallized from ethyl acetate).

EXAMPLE 10

3-{4-[2-(Fluorenyl-(9)-acetamido)-ethyl]-phenyl}-butyric acid 11.8 g. 4'-[2-(Fluorenyl-(9)-acetamido)-ethyl]-acetophenone (m.p. 180°–182° C.) are suspended in 30 ml. dimethyl formamide and to this a mixture of 9.6 g. triethyl phosphonoacetate, 7.5 g. 30% sodium methylate solution and 7 ml. dimethyl formamide is added dropwise at ambient temperature over the course of half an hour. The reaction mixture is then warmed to 40°–45° C. for 6 hours, subsequently poured on to ice and filtered off with suction. The ethyl 3-{4-[2-(fluorenyl-(9)-acetamido)-ethyl]-phenyl}-but-2-enoate thus obtained can be recrystallized from methylene chloride:ligroin (1:1); m.p. 156°–158° C.; yield 80% of theory.

10.6 g. Ethyl 3-{4-[2-(fluorenyl-(9)-acetamido)-ethyl]-phenyl}-but-2-enoate are hydrogenated in 150 ml. methanol with hydrogen at atmospheric pressure and ambient temperature in the presence of 1 g. palladium-charcoal. After the take up of 600 ml. hydrogen, the catalyst is filtered off with suction and the solvent is stripped off in a vacuum. There is thus obtained, in a yield of 94% of theory, ethyl 3-{4-[2-(fluorenyl-(9)-acetamido)-ethyl]-phenyl}-butyrate; m.p. 103°–105° C.

10.0 g. of this ester are boiled under reflux for 2 hours in 50 ml. 80% ethanol with 1.3 g. sodium hydroxide and then evaporated. The residue is taken up in water, filtered and the filtrate acidified. The initially greasy product obtained is recrystallized twice from 80% isopropanol. There is obtained 3-{4-[2-(fluorenyl-(9)- acetamido)-ethyl]-phenyl}-butyric acid in a yield of 57% of theory; m.p. 138°-140° C.

EXAMPLE 11

N-{3-{4-[2-(Fluorenyl-(9)-acetamido)-ethyl]-phenyl}-propionyl}-β-alanine 4.6 ml. triethylamine and 1.8 ml. ethyl chloroformate are successively added dropwise at −10° C. to 6.0 g. 3-{4-[2-(fluorenyl-(9)-acetamido)-ethyl]-phenyl}-propionic acid in 80 ml. anhydrous methylene chloride, the reaction mixture is then stirred for 30 minutes, 2.8 g. ethyl β-alanine hydrochloride are added thereto and then the reaction mixture is warmed to 40° C. for 5 hours. The solution is subsequently successively washed with 2N hydrochloric acid, 2N aqueous sodium hydroxide solution and water and then dried and evaporated. There is thus obtained ethyl N-{3-{4-[2-(fluorenyl-(9)-acetamido)-ethyl]-phenyl}-propionyl}-β-alanine, which is recrystallized from ethanol. Yield 3.4 g. (45.5% of theory); m.p. 203°-204° C.

3.3 g. of this ester are heated under reflux for 3 hours with a solution of 0.8 g. potassium hydroxide in 30 ml. ethanol. The reaction mixture is then cooled, the potassium salt of the desired acid thereby precipitating out. This is filtered off with suction, washed with a little ethanol, dissolved in water and the solution treated with active charcoal and acidified. The desired free carboxylic acid is filtered off with suction and, for purification, again dissolved in a very dilute aqueous solution of potassium hydroxide, the solution is treated with active charcoal and, by acidification with hydrochloric acid, N-{3-{4-[2-(fluorenyl-(9)-acetamido)-ethyl]-phenyl}-propionyl}-β-alanine again precipitated out. Yield 1.0 g. (32% of theory); m.p. 254°-255° C.

In an analogous manner, by the use of 4-[2-(fluorenyl-(9)-acetamido)-ethyl]-benzoic acid and L-alanine ethyl ester hydrochloride, there is obtained ethyl N-{4-[2-(fluorenyl-(9)-acetamido)-ethyl]-benzoyl}-L-alanine; m.p. 180°-184° C. (recrystallized from methylene chloride) and from this, by saponification N-{4-[2-(fluorenyl-(9)-acetamido)-ethyl]-benzoyl}-L-alanine; m.p. 174°-177° C. (recrystallized from ethyl acetate).

EXAMPLE 12

3-{4-[2-(3-Hydroxyfluorenyl-(9)-acetamido)-ethyl]-phenyl}-propionic acid 1.5 g. 3-{4-[2-(3-Methoxy-fluorenyl-(9)-acetamido)-ethyl]-phenyl}-propionic acid are heated under reflux for 3 hours with a mixture of 11 ml. glacial acetic acid and 11 ml. 47% hydrobromic acid. The reaction mixture is thereafter poured on to ice and the product is shaken out with methylene chloride. The solvent is evaporated and the residue is dissolved in very dilute aqueous sodium hydroxide solution, treated with active charcoal and acidified with dilute hydrochloric acid in order to precipitate out the free carboxylic acid. Yield 0.7 g. (48% of theory); m.p. 86°-89° C.

EXAMPLE 13

4-[2-(Fluorenyl-(9)-acetamido)-ethyl]-benzyl alcohol

A solution of fluorenyl-(9)-acetyl chloride (prepared from 2.2 g. fluorenyl-(9)-acetic acid and 3 ml. thionyl chloride under reflux) in 12 ml. methylene chloride is added dropwise at 0° C. to 1.9 g. 4-(2-aminoethyl)-benzyl alcohol hydrochloride (m.p. 151°-155° C.) (decomp.) in 10 ml. 2N aqueous sodium hydroxide solution. The reaction mixture is then stirred for 2 hours at ambient temperature. The product is sparingly soluble in water and methylene chloride and precipitates out. The methylene chloride is evaporated off by heating, the solid substance is filtered off with suction, taken up in ethyl acetate and the solution successively washed with 1N hydrochloric acid and 1N aqueous sodium hydroxide solution, then dried, treated with active charcoal and evaporated. The crude product (yield 2.4 g.; 69.5% of theory; m.p. 168°-171° C.) is purified by recrystallizing twice from ethylene chloride and once from a little ethyl acetate. Yield of the desired compound 1.1 g. (32% of theory); m.p. 176°-178° C.

EXAMPLE 14

4-[2-(Fluorenyl-(9)-acetamido)-ethyl]-benzaldehyde

Fluorenyl-(9)-acetyl chloride is prepared from 3.6 g. fluorenyl-(9)-acetic acid and 4 ml. thionyl chloride by heating under reflux for 2 hours. It is dissolved in 20 ml. methylene chloride and this solution is added dropwise at 0° C. to 3.0 g. 4-(2-aminoethyl)-benzaldehyde hydrochloride (m.p. > 300° C.) and 32 ml. 1N aqueous sodium hydroxide solution. The reaction mixture is stirred for half an hour, while cooling with ice, and then for 2 hours at ambient temperature. The two layers are then separated and the aqueous phase is again shaken out with methylene chloride. The combined organic phases are successively washed with a dilute aqueous solution of sodium hydroxide and dilute hydrochloric acid, then dried and the methylene chloride evaporated. The product obtained is purified by chromatography over a silica gel column with xyleno:methyl ethyl ketone (1:1). Yield 2.7 g. (48% of theory); m.p. 140°-143° C.

The novel compounds may be administered by themselves or in conjunction with carriers which are pharmacologically acceptable, either active or inert. The dosage units are similar to those of the heretofore known anti-cholesterol agents, e.g., about 0.2 to 2 grams per day for an adult or about 3-30 mg/kg per day although higher or lower dosages can be used. Rather than a single dose it is preferable if the compounds are administered in the course of a day, i.e., about four applications of 100 mg. each at spaced time intervals or 8 of about 50 mg. each. A convenient form of administration is in a gelatine capsule.

The dosage of the novel compounds of the present invention for the treatment of diabetes depends in the main on the age, weight, and condition of the patient being treated. The preferable form of administration is via the oral route in connection with which dosage units containing 30-200 mg. of active compound in combination with a suitable pharmaceutical diluent is employed. One or two unit dosages are good from one to four times a day.

For the preparation of pharmaceutical compositions, at least one of the new compounds (I) is mixed with a solid or liquid pharmaceutical carrier or diluent and optionally with an odoriferous, flavoring and/or coloring material and formed, for example, into tablets or dragees, or with the addition of appropriate adjuvants, suspended or dissolved in water or in an oil, for example, olive oil.

The hypoglycaemic activity of the test compounds was tested in known manner as follows:

The test compounds were administered to male Sprague-Dawley rats with a body weight of 200-220 g by intraperitoneal injection (i.p.) as a solution of the potassium salt or per os (p.o.) as a Tylose suspension.

The test compounds were administered to rabbits either by intravenous injection (i.v.) into the ear edge vein as a solution of the potassium salt or per os through a stomach tube as a Tylose suspension.

In the following table, there is given the threshold dosage in mg/kg of body weight, i.e. the lowest dosage of compound required to produce a significant reduction in the blood sugar level, viz. about 15–20%.

For purposes of comparison, $N_1$-(sulfanilyl)-$N_2$-(n-butyl)-urea (sold under trade name "Nadisan") was tested under the same conditions.

The results are set forth in the following table:

TABLE

| Example | Threshold dosage, mg/kg | |
|---|---|---|
| | Rats | Rabbits |
| Nadisan* | 25 i.p. | 200 i.v. |
| 1/1a** | 10–25 i.p. | 5 i.v. |
| 1/1b | 25 i.p. | 25 i.v. |
| 1/1c | 25 i.p. | 0,5 i.v. |
| | 2.5–5 p.o. | 1.0 p.o. |
| 1/1e | 2.5 i.p. | 1.0 i.v. |
| (also 5a, 5b) | 10 p.o. | 2.5 p.o. |
| 1/1f | 25 i.p. | 10 i.v. |
| 1/1g | 25 i.p. | 10 i.v. |
| 1/1h | 1.0–2.5 i.p. | 0.5 i.v. |
| | 5 p.o. | 1.0–2.5 p.o. |
| 1/2a | 25 i.p. | 5 i.v. |
| 1/2b | 25 i.p. | 25 i.v. |
| 1/2c | 10–25 i.p. | 25 i.v. |
| 1/2d | 25 i.p. | 10 i.v. |
| 1/2e | 5–10 i.p. | 0.5–1.0 i.v. |
| 1/4 | 25 i.p. | 25 i.v. |
| 1/6 | 10–25 i.p. | 5 i.v. |
| 1/7 (also 6) | 2.5 i.p. | 1.0 i.v. |
| | 25 p.o. | 2.5 p.o.) |
| 1/9a | 2.5 i.p. | 0.25 i.v. |
| | 2.5 p.o. | 0.25–0.5 p.o. |
| 1/9b | 2.5 i.p. | 0.5 i.v. |
| | 10 p.o. | 1.0–2.5 p.o. |
| 1/10 | 5 i.p. | 1.0 i.v. |
| 1/11 | 25 i.p. | 10 i.v. |
| 2a (also 7) | 2.5 i.p. | 0.5–1.0 i.v. |
| | 5 p.o. | 1.0–2.5 p.o. |
| 3/1a | 10–25 i.p. | 10–25 i.v. |
| 3/2a | 25 i.p. | 25 i.v. |
| 3/2b | 25 i.p. | 25 i.v. |
| 3/2c | 5 i.p. | 1.0 i.v. |
| | 10 p.o. | 2.5 p.o. |
| 3/3 | 2.5 i.p. | 0.5 i.v. |
| 4a | 25 i.p. | 10 i.v. |
| 5 | 5 i.p. | 1.0 i.v. |
| | 5 p.o. | 5 p.o. |
| 9/1a | 10–25 i.p. | 5 i.v. |
| 9/2 | 1.0–2.5 i.p. | 0.25–0.5 i.v. |
| | 2.5 p.o. | 5 p.o. |
| 9/3 | 1.0–2.5 i.p. | 0.25–0.5 i.v. |
| | 2.5 p.o. | 0.5–1.0 p.o. |
| 10 | 25 i.p. | 10 i.v. |
| 13 | 25 p.o. | 5–10 p.o. |
| 14 | 25 p.o. | 2.5 p.o. |

*Nadisan = $N_1$-(sulfanilyl)-$N_2{}^1$-(n-butyl)-urea
**Here and in all instances the compound tested was the final product, viz. the acid, except Example 13 which is an alcohol and Example 14 which is an aldehyde.

It will be appreciated that the instant specification and examples are set forth by way of illustration and not limitation, and that various modifications and changes may be made without departing from the spirit and scope of the present invention.

What is claims is

1. An N-substituted carboxylic acid amide of the formula

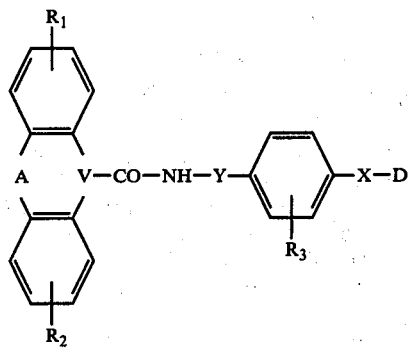

where
A is a valency bond or a methylene, ethylene or vinylene radical,
V is a trivalent hydrocarbon radical containing up to 4 carbon atoms,
$R_1$ and $R_2$ each independently is hydrogen, a halogen atom, a hydroxyl group or an alkyl or alkoxy radical,
$R_3$ is hydrogen, a hydroxyl group or an alkoxy radical,
Y is an alkylene radical containing up to 3 carbon atoms,
X is a valency bond or a divalent aliphatic hydrocarbon radical containing up to 6 carbon atoms, and
D is a free or esterified carboxyl radical,
or a physiologically compatible salt thereof.

2. A compound according to claim 1, wherein
V is a radical selected from the group consisting of

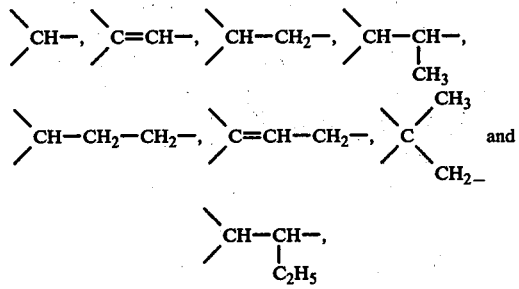

$R_1$ and $R_2$ each independently is hydrogen, fluorine, chlorine, bromine, a hydroxyl group, or an alkyl or alkoxy radical containing up to 5 carbon atoms,
$R_3$ is hydrogen, a hydroxyl group, or an alkoxy radical containing up to 5 carbon atoms,
X is a valency bond or a divalent aliphatic hydrocarbon radical containing up to 4 carbon atoms,
D is a carboxyl, carboalkoxy radical wherein the alkoxy radical has up to 4 carbon atoms.

3. A compound according to claim 1, wherein A is a methylene, ethylene or vinylene radical.

4. A compound according to claim 1, wherein $R_3$ is a hydroxyl group or an alkoxy radical containing up to 5 carbon atoms.

5. A compound according to claim 1, wherein X is a valency bond.

6. A compound according to claim 1, wherein X is $-CH_2-CH_2-$.

7. A compound according to claim 1, wherein D is a hydroxymethyl or formyl radical.

8. A compound according to claim 1, wherein D is a carboalkoxy radical wherein the alkoxy radical has up to 4 carbon atoms.

9. A compound according to claim 1, wherein such compound is 3-{4-[2-(3-methylfluorenyl-(9)-acetamido)-ethyl]-phenyl}-propionic acid.

10. A compound according to claim 1, wherein such compound is 3-{4-[2-(2-{fluorenyl-(9)}-propionamido)-ethyl]-phenyl}-propionic acid.

11. A compound according to claim 1, wherein such compound is 2-methoxy-4-[2-(fluorenyl-(9)-acetamido)-ethyl]-benzoic acid.

12. A compound according to claim 1, wherein such compound is 4-[2-(fluorenyl-(9)-acetamido)-ethyl]-benzoic acid.

13. A compound according to claim 1, wherein such compound is 4-{2-(2-[fluorenyl-(9)]-propionamido)-ethyl]-benzoic acid.

14. A hypoglycaemic or hypolipidaemic composition of matter comprising a hypoglycaemically or hypolipidaemically effective amount of a compound according to claim 1 in admixture with a pharmacologically acceptable diluent.

15. A method for lowering the sugar or lipid level in the blood of a patient which comprises administering to such patient a hypoglycaemically or hypolipidaemically effective amount of a compound according to claim 1.

16. The method according to claim 15, wherein such compound is
3-{4-[2-(3-methylfluorenyl-(9)-acetamido)-ethyl]-phenyl}-propionic acid,
3-{4-[2-(2-{fluorenyl-(9)}-propionamido)-ethyl]-phenyl}-propionic acid,
2-methoxy-4-[2-(fluorenyl-9)-acetamido)-ethyl]-benzoic acid,
4-[2-(fluorenyl-(9)-acetamido)-ethyl]-benzoic acid, or
4-{2-(2-[fluorenyl-(9)]-propionamido)-ethyl}-benzoic acid,
or a physiologically compatible salt thereof.

* * * * *